United States Patent
Lee et al.

(10) Patent No.: US 7,638,493 B2
(45) Date of Patent: Dec. 29, 2009

(54) ARTIFICIAL PULMONARY SURFACTANT COMPOSITIONS AND USE OF THE SAME

(76) Inventors: Sannamu Lee, 1-8-5-410, Meinohama-Eki-Minami, Nishi-ku, Fukuoka-shi, Fukuoka 819-0006 (JP); Ko Yukikate, 3-10-5-1503, Yakuin, Chuo-ku, Fukuoka-shi, Fukuoka 810-0022 (JP); Yoshihiro Nakamura, C/O Muromachi Chemical Co., Ltd., 1-38-5, Shinkatsutachi-machi, Omuta-shi, Fukuoka 836-0895 (JP)

( * ) Notice: Subject to any disclaimer, the term of this patent is extended or adjusted under 35 U.S.C. 154(b) by 293 days.

(21) Appl. No.: 11/587,901

(22) PCT Filed: Apr. 28, 2005

(86) PCT No.: PCT/JP2005/008234
§ 371 (c)(1),
(2), (4) Date: Oct. 27, 2006

(87) PCT Pub. No.: WO2005/105111
PCT Pub. Date: Nov. 10, 2005

(65) Prior Publication Data
US 2008/0194458 A1    Aug. 14, 2008

Related U.S. Application Data

(60) Provisional application No. 60/566,088, filed on Apr. 29, 2004.

(51) Int. Cl.
*A61K 38/00* (2006.01)

(52) U.S. Cl. .................... 514/12; 514/13; 530/324; 530/325; 530/326; 530/327; 530/329

(58) Field of Classification Search ............... 514/12, 514/13; 530/324–329
See application file for complete search history.

(56) References Cited

U.S. PATENT DOCUMENTS

| 4,312,860 A | 1/1982 | Clements |
| 5,827,825 A * | 10/1998 | Takei et al. .................... 514/12 |
| 6,613,734 B2 * | 9/2003 | Cochrane et al. ............... 514/2 |

FOREIGN PATENT DOCUMENTS

| JP | 57-099524 A | 6/1982 |
| WO | WO-95/15980 A1 | 6/1995 |

OTHER PUBLICATIONS

Nanaumi et al., Nihon Kaimen Igakukai Zasshi, Oct. 5, 1999, vol. 30, No. 1/2, pp. 67-75.

\* cited by examiner

*Primary Examiner*—Tekchand Saidha
(74) *Attorney, Agent, or Firm*—Birch, Stewart, Kolasch & Birch, LLP

(57) ABSTRACT

The artificial pulmonary surfactant composition according to the present invention comprises a lipid mixture system containing no protein or peptide or a protein/peptide-lipid mixture prepared by adding a protein or a peptide to the above lipid mixture system. The artificial pulmonary surfactant composition of this invention is useful for RDS and ARDS as well as for the mitigation or prevention of respiratory insufficiencies caused by pneumonia, respiratory difficulties caused by asthma, etc. and it can be prepared at lower costs.

10 Claims, 7 Drawing Sheets

Hel 13-5 : NH$_2$-KLLKLLLKLWLKLLKLLL-COOH

Hel 11-7 : NH$_2$-KLLKLLLKLWKKLLKLLK-COOH

Hel 7-11 : NH$_2$-KKLKLLKKLWKKLLKLK-OH

P$_{24}$ : AcNH-K$_2$GL$_{24}$K$_2$A-CONH$_2$

Hel 7-11-P$_{24}$ : AcNH-KKLKKLLKKWKLLKKLKG$_3$K$_2$GL$_{24}$K$_2$A-CONH$_2$

KL$_4$ : NH$_2$-KLLLLKLLLLKLLLLKLLLLK-COOH

1: Surfacten    2: OD (85%), PA (15%)
3: OD (35%), phosphatidylcholine (40%), PA (25%)
4: OD (35%), egg yolk lecithin (40%), PA (25%)
5: Phosphatidylcholine (85%), PA (15%)
6: OD (30%), phosphatidylcholine (35%), PA (25%), cholesterol (10%)
7: OD (25%), phosphatidylcholine (40%), PA (25%), triglycerol (10%)
8: OD (30%), phosphatidylcholine (35%), PA (15%), cholesterol (10%), triglycerol (10%)

1: Surfacten   2: OD (70%), phosphatidylcholine (10%), PA (20%)
3: OD (40%), phosphatidylcholine (40%), PA (20%)
4: OD (10%), phosphatidylcholine (70%), PA (20%)
5: OD (80%), phosphatidylcholine (10%), PA (10%)
6: OD (40%), phosphatidylcholine (50%), PA (10%)

1: Surfacten
2: OD (85%), PA (15%), Peptide Hel7-11-P24 (5%)
3: OD (35%), phosphatidylcholine (40%), PA (20%), Peptide Hel7-11-P24 (5%)
4: OD (35%), phosphatidylcholine (40%), PA (20%), Peptide Hel7-13-5 (5%)
5: OD (35%), phosphatidylcholine (40%), PA (10%), Peptide KL4 (5%)

1: Exosurf   2: KL4 (Surfaxin)
3: Hydrogenated soy lecithin PC70H (40%), soy lecithin PC70 (40%), PA (20%)
4: Hydrogenated soy lecithin PC70H (40%), soy lecithin PC70 (40%), PA (20%)
5: Hydrogenated soy lecithin PC70H (40%), soy lecithin PC70 (40%), PA (17.5%), Peptide Hel13-5 (2.5%)
6: Hydrogenated soy lecithin PC70H (40%), soy lecithin PC70 (40%), PA (17.5%), Peptide Hel13-5 (2.5%)

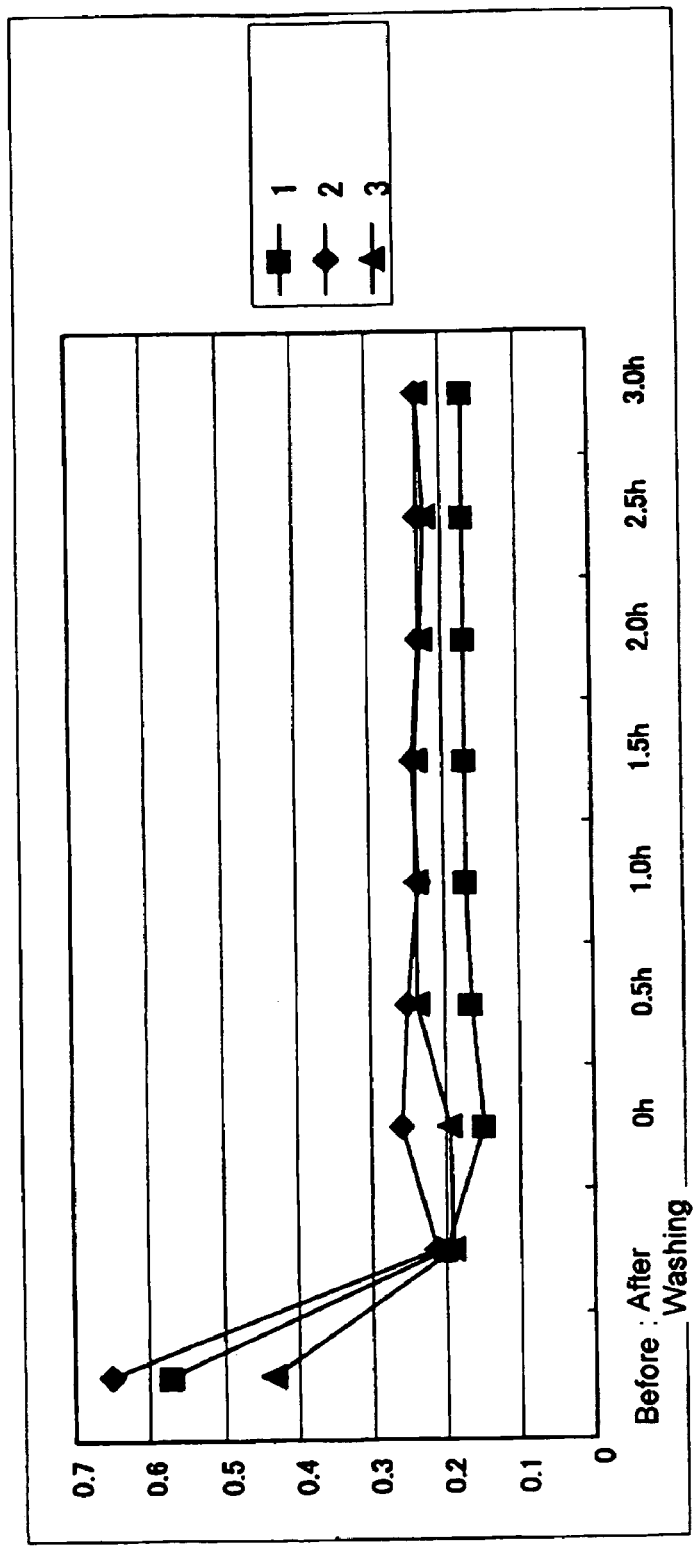

SEQUENCE LISTING

```
<160> NUMBER OF SEQ ID NOS: 6

<210> SEQ ID NO 1
<211> LENGTH: 18
<212> TYPE: PRT
<213> ORGANISM: Artificial Sequence
<220> FEATURE:
<223> OTHER INFORMATION: Synthethic peptide

<400> SEQUENCE: 1

Lys Leu Leu Lys Leu Leu Leu Lys Leu Trp Leu Lys Leu Leu Lys Leu
1               5                   10                  15

Leu Leu

<210> SEQ ID NO 2
<211> LENGTH: 18
<212> TYPE: PRT
<213> ORGANISM: Artificial Sequence
<220> FEATURE:
<223> OTHER INFORMATION: Synthethic peptide

<400> SEQUENCE: 2

Lys Leu Leu Lys Leu Leu Leu Lys Leu Trp Lys Lys Leu Leu Lys Leu
1               5                   10                  15

Leu Lys

<210> SEQ ID NO 3
<211> LENGTH: 18
<212> TYPE: PRT
<213> ORGANISM: Artificial Sequence
<220> FEATURE:
<223> OTHER INFORMATION: Synthethic peptide

<400> SEQUENCE: 3

Lys Lys Leu Lys Lys Leu Leu Lys Lys Trp Lys Lys Leu Leu Lys Lys
1               5                   10                  15

Leu Lys

<210> SEQ ID NO 4
<211> LENGTH: 30
<212> TYPE: PRT
<213> ORGANISM: Artificial Sequence
<220> FEATURE:
<223> OTHER INFORMATION: Synthethic peptide

<400> SEQUENCE: 4

Lys Lys Gly Leu Leu Leu Leu Leu Leu Leu Leu Leu Leu Leu Leu Leu
```

-continued

```
                1               5                  10                 15
Leu Leu Leu Leu Leu Leu Leu Leu Leu Leu Leu Lys Lys Ala
                    20                 25                  30

<210> SEQ ID NO 5
<211> LENGTH: 51
<212> TYPE: PRT
<213> ORGANISM: Artificial Sequence
<220> FEATURE:
<223> OTHER INFORMATION: Synthethic peptide

<400> SEQUENCE: 5

Lys Lys Leu Lys Lys Leu Leu Lys Lys Trp Lys Lys Leu Leu Lys Lys
1               5                  10                 15

Leu Lys Gly Gly Gly Lys Lys Gly Leu Leu Leu Leu Leu Leu Leu Leu
                    20                 25                  30

Leu Leu Leu Leu Leu Leu Leu Leu Leu Leu Leu Leu Leu Leu Leu
            35                 40                  45

Lys Lys Ala
        50

<210> SEQ ID NO 6
<211> LENGTH: 21
<212> TYPE: PRT
<213> ORGANISM: Artificial Sequence
<220> FEATURE:
<223> OTHER INFORMATION: Synthethic peptide

<400> SEQUENCE: 6

Lys Leu Leu Leu Leu Lys Leu Leu Leu Leu Lys Leu Leu Leu Leu Lys
1               5                  10                 15

Leu Leu Leu Leu Lys
            20
```

ARTIFICIAL PULMONARY SURFACTANT COMPOSITIONS AND USE OF THE SAME

This application is the U.S. National Phase of PCT/JP2005/008234, filed Apr. 29, 2005, which claims priority to U.S. Provisional Application No. 60/566,088, filed Apr. 29, 2004. The above are all incorporated by reference.

TECHNICAL FIELD

The present invention relates to an artificial pulmonary surfactant composition and use of the same. More particularly, the present invention relates to an artificial pulmonary surfactant composition and a method for use thereof, which has a novel chemical formulation, which is useful as an agent for curing respiratory distress syndromes and the like, and which can be prepared at lower costs.

BACKGROUND TECHNOLOGY

Currently, as an agent for curing respiratory distress syndrome (RDS) having a high mortality and acute respiratory distress syndrome (ARDS) causing severe respiratory disorders, there is applied an artificial pulmonary surfactant prepared from the pulmonary surfactant ingredient secreted from the bovine lung (e.g., "Pulmonary Surfactants Now" edited by Yoshida, S., Shinko Koeki Isho Shuppanbu, Tokyo, 1990; Riodan, J. R.: Molecular Basis of Disease: Pulmonary Surfactant, ed., Biochem. Biophys. Acta, 1408, 77-363, 1998).

The pulmonary surfactant is a lipid-protein complex produced by the aveolar cells and secreted therefrom, which is a substance essential for the maintenance of life and which plays a role for the pulmonary function by reducing the surface tension of the alveoli. The pulmonary surfactant present in the alveoli is composed of approximately 10% of proteins and lipid ingredients consisting mainly of phospholipids (e.g., Veldhuizen, R., et al., Biochim. Biophys. Acta, 1408, 90-108, 1998). The pulmonary surfactant contains the lipids, particularly a neutral phospholipid, i.e., L-(-phosphatidylcholine (PC) which amounts to 80.5% of the total lipids; while L-(-phosphatidylglycerol (PG) which is an acidic lipid amounts to 9.1%, L-α-phosphatidylinositol (PI) to 2.6% and cholesterol to 7.3%. In particular, it is to be noted that dipalmitoyi-L-α-phosphatidylcholine (DPPC) composed of saturated alkyl groups amounts to 47.7%, that is, approximately a half of the PC, and that this is considered to be a factor of preventing a collapse of the lung. It is rendered evident, however, that only the phospholipids including DPPC do not have any surfactant activity and small amounts of the protein ingredients are of importance (e.g., Robertson, B., and Halliday, H. L., Biochim. Biophys. Acta, 1408, 341-362, 1998).

There is an increasing necessity of the pulmonary surfactant for the application not only to RDS and ADRS but also to inflammatory pulmonary diseases such as pneumonia, etc. as well as to the mitigation of severe respiratory insufficiency symptoms caused by pulmonary cancers, etc., which are recently causing a rapidly increasing mortality. It is also known that the pulmonary surfactant substance is being secreted from the bronchus, and the substance is considered to play a role as an expectorant by preventing the block of the peripheral airway (e.g., Liu M., et al., J. Appl. Physiol., 71, 742-748, 1991). The pulmonary surfactant is expected to be applied to various diseases that require improvements in respiratory disorders because, for example, the inhalation of the pulmonary surfactant can relieve a fit of allergy-induced asthma (e.g., Babu, K. S., et al., Eur. Respir. J., 21:1046-1049, 2003).

Fujiwara et al. have reported about an effect of the artificial pulmonary surfactant on human RDS and succeeded for the first time in the world in the development of an agent for curing RDS ("Surfacten®") (e.g., Japanese Patent Publication No. S61-9925). Surfacten® is an agent which consists of phospholipids (75.0-95.5%), neutral lipids (1.8-14.0%) and proteins (5% or less), which is prepared by extracting the active pulmonary surfactant ingredient from the bovine lung. As the protein and the phospholipid (particularly DPPC) to be used therefor are expensive, the resulting pulmonary surfactant, Surfacten®, is also so expensive that the issue is a difficulty in the application of Surfacten® to a very limited field.

The incidence of ARDS is reported to be 15 to 20 cases out of the population of 100,000. Even if the basic diseases could be cured, however, it is also reported that the exitus may unfortunately be caused to occur in many cases due to damages of the lung caused by the artificial ventilation or oxygen used for the treatment in the acute stage and the mortality of ARDS is as extremely high as approximately 50%. It is further reported that the administration of large amounts of the artificial pulmonary surfactant at the early stage of ARDS can improve the pulmonary functions and minimizing the damages of the lung reducing the mortality up to 20% (e.g., Gregory, T. J., et al., Am. J. Respir. Crit. Car. Med., 155, 1309-1315, 1997). The pulmonary surfactant is of great significance for the treatment of severe respiratory insufficiency and at the same time it is effective for removing phlegm and relieving a fit of asthma in the manner as described above.

From the above, many medical doctors involved in the treatment of respiratory diseases have pointed out the possibilities of application of the pulmonary surfactant to many different kinds of pulmonary diseases; however, the pulmonary surfactant is so very expensive that the application of Surfacten® to RDS only is currently covered by the health insurance in Japan. A further issue is that Surfacten® is a bovine protein preparation so that it still has the possibility of infection due to its antigenicity and unknown antigenicity and the problem with bovine spongiform encephalopathy for example still remains unsolved. In this sense, the development of an artificial pulmonary surfactant which can be prepared at lower costs and has no side effects has been demanded.

In order to meet such a demand, Cochrane et al. reported a synthetic surfactant for the first time in 1991 (e.g., Cochrane C. G. and Revak S. D., Science, 254, 566-568, 1991). The synthetic surfactant which in turn is currently under clinical investigation is a lipid-peptide complex (Surfaxin) composed of 21 amino acids (KL4) and a lipid and is expected to become a novel agent for the treatment of ARDS (e.g., Wiswell, T., et al., Pediatrics, 109, 1081-1087, 2002).

In addition, there are disclosed a pulmonary surfactant composed of a mixture of a synthetic peptide with a lipid and an agent for the treatment of respiratory distress syndromes which contains the pulmonary surfactant as an active ingredient (e.g., Japanese Patent Application Publication No. 05-294,996; WO 95/15,980). More specifically, the pulmonary surfactant is composed of choline phosphoglyceride, a synthetic peptide having a particular amino sequence, an acidic phospholipid and an aliphatic acid.

DISCLOSURE OF THE INVENTION

As a result of an extensive review and studies on artificial pulmonary surfactant compositions which do not contain a protein or peptide as an essential ingredient and can be prepared at lower costs, it has been found by the present inventors that an artificial pulmonary surfactant composition consisting of a novel combination of a mixture of lipids available at lower costs had a surfactant activity as high as commercially available Surfacten®. As a result of further studies, it has also been found that a peptide-lipid mixture system prepared by the addition of a peptide to the above lipid mixture system had a surface activity and a surfactant activity in the lung of an animal as high as Surfacten®. The present invention has been completed on the basis of these findings.

As the artificial pulmonary surfactant composition according to the present invention can be prepared at lower costs, it has the possibility that it can be applied to a wide variety of diseases involving a surfactant deficiency or functional insufficiency, etc., that is, not only to RDS and ARDS, but also to the mitigation and prevention of disorders of respiratory functions caused by acute pneumonia, pulmonary cancers, asthma and so on as well as to the removal of phlegm caused by pneumonia, a cold and so on.

Therefore, the present invention has the object to provide an artificial pulmonary surfactant composition consisting of a lipid mixture system containing neither protein nor peptide and composed of a combination of lipids prepared at lower costs or consisting of a protein/peptide-lipid mixture system in which a protein or a peptide is added to a lipid mixture system, the artificial pulmonary surfactant composition being effective for diseases such as acute pulmonary diseases, etc. which are associated with a deficiency of a surfactant or a function insufficiency, etc. and which can be prepared at lower costs.

The present invention has also the object to provide a method of the use of the artificial pulmonary surfactant composition for the treatment or prevention of diseases associated with a surfactant deficiency or a function insufficiency.

In order to achieve the above objects, the present invention provides an artificial pulmonary surfactant composition that is composed of a lipid mixture system containing no protein or peptide and which can be prepared at lower costs.

The present invention has also the object to provide an artificial pulmonary surfactant composition which consists of a peptide-lipid mixture system and can be prepared at lower costs.

The present invention in an embodiment provides an artificial pulmonary surfactant composition containing a phospholipid, a higher alcohol and a higher aliphatic acid as major ingredients. The present invention in a preferred embodiment provides an artificial pulmonary surfactant composition consisting of the phospholipids at the rate of from approximately 20% to 60% by weight, preferably from approximately 30% to 50% by weight, the higher alcohol at the rate of from approximately 30% to 70% by weight, preferably from approximately 40% to 60% by weight, and the higher aliphatic acid at the rate of approximately 1 to 30%, preferably from approximately 5% to 20%, each with respect to the total dry weight.

The present invention in another aspect provides an artificial pulmonary surfactant composition further containing a peptide at the rate of from approximately 2% to 10%, preferably from 1% to 5%.

The present invention in a further aspect provides a method of the use of the artificial pulmonary surfactant composition which comprises applying the artificial pulmonary surfactant composition to diseases involving a surfactant deficiency or a function insufficiency, which include, for example, RDS, ADRS, acute pneumonia, pulmonary cancers, asthma and so on, as well as to the mitigation and prevention of disorders of respiratory functions or the removal of phlegm caused by pneumonia, a cold and so on.

The other objects, features and other embodiments of the present invention will become apparent in the course of the description as will follow, with reference to the accompanying drawings.

BRIEF DESCRIPTION OF THE ACCOMPANYING DRAWINGS

FIG. 5b shows an illustration indicating the result of an experiment for the recovery of the pulmonary function using rats with the lung irrigated.

DESCRIPTION OF THE BEST MODES FOR CARRYING OUT THE INVENTION

Figure 1:
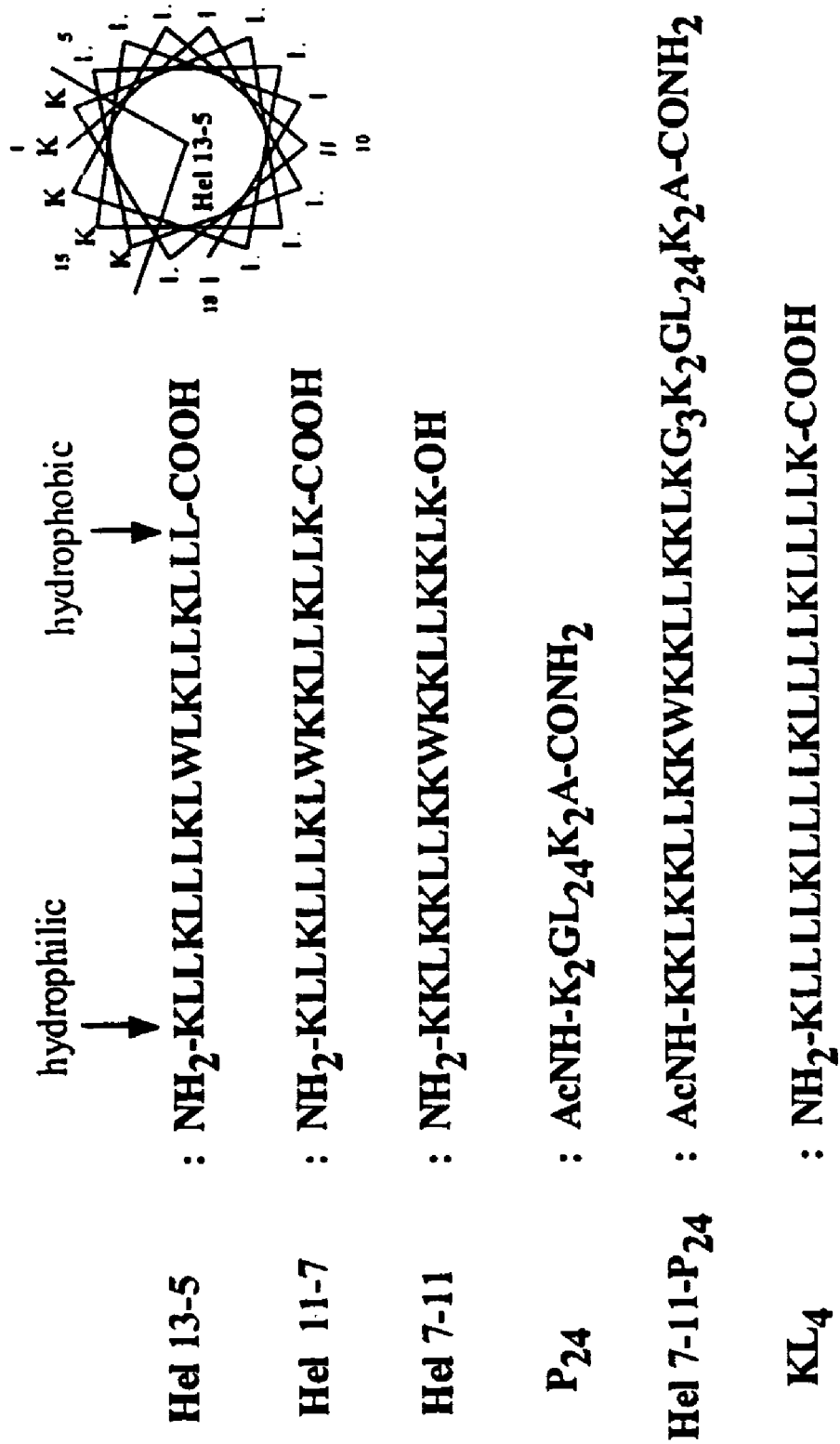
FIG. 1 shows a schematic representation of one-dimensional chemical structures of various synthetic pulmonary surfactant peptides (SEQ ID NOS: 1-6).

In accordance with the present invention, it is needed to form a stable single molecular membrane and a bimolecular membrane in order to consider the mechanism of transcription of the pulmonary surfactant activity. It has been considered to be essential to use the phospholipids to form an equilibrium between the single molecular membrane and the bimolecular membrane upon an increase or decrease of the pulmonary pressure. Further, in order to prevent a collapse of the lung at the time of the compression of the lung, the presence of the phospholipids, particularly DPPC, is considered to be essential. Further, a small amount of PG is also considered to be needed.

The conventional artificial pulmonary surfactant composition using DPPC has the big drawback that the scope of application is very limited because DPPC is so expensive that the resulting artificial pulmonary surfactant composition results to a very expensive one. Therefore, as the present invention uses an alternative material for the DPPC and it does not require the use of expensive DPPC or, even if DPPC is used as needed, the amount of the DPPC can be limited to a minimal amount, the present invention has an extremely great merit. Such an alternative material may include a phospholipid such as, for example, egg PC extracted and purified from relatively less expensive egg yolks or egg yolk lecithin or soy lecithin or fractional soy lecithin available at lower costs. As an alternative material to be used for the DPPC having a saturated alkyl chain, there may be used, for example, a saturated higher alcohol (e.g., 1-octadecanol, OD) and hydrogenated lecithin prepared by hydrogenating the unsaturated aliphatic chain of the fractional soy lecithin. As the acidic ingredient, there may be used a higher aliphatic acid (e.g., palmitic acid (PA), stearic acid, etc.) which has been frequently used as the lipid for the conventional artificial pulmonary surfactant. In addition, a neutral lipid (e.g., triacylglycerol, cholesterol, saponin, etc.) may also be used.

The artificial pulmonary surfactant composition according to the present invention is characterized by a lipid mixture system composed of the phospholipid, higher alcohol and higher aliphatic acid as the major ingredients or a protein/peptide-lipid mixture system composed of a combination of the lipid mixture system to which a protein or peptide is added.

As the phospholipids to be used for the artificial pulmonary surfactant composition according to the present invention, there may be mentioned, for example, egg yolk lecithin, soy lecithin or lecithins extracted from other natural sources, hydrogenated lecithin prepared by hydrogenating the unsaturated aliphatic chain of fractional soy lecithin, or phosphatidylcholines such as DPPC, etc. The rate of the phospholipid may be in the range of from approximately 20% to 60% by weight, preferably from approximately 30% to 50% by weight, with respect to the total dry weight. As the phosphatidylcholines other than DPPC to be used for the present invention, there may be used, for example, a diacylphosphatidylcholine having an acyl group with 12 to 24 carbon atoms, preferably having two saturated acyl groups, including, but being not limited to, distearoylphosphatidylcholine, palmitoylstearoylphosphatidylcholine, etc. Further, there may be used other phosphatidylcholines including, but being not limited to, a diacylphosphatidylcholine, an alkylacylphosphatidylcholine such as, e.g., hexadecylpalmitoylphosphatidylcholine, octadecylpalmitoylphosphatidylcholine, etc., and a dialkylphosphatidylcholine such as, e.g., dihexadecylphosphatidylcholine, etc.

As the higher alcohol, there may be mentioned, for example, a saturated or unsaturated aliphatic alcohol having from 14 to 20 carbon atoms or a saturated or unsaturated, higher aliphatic amine having from 14 to 20 carbon atoms. The saturated higher alcohol including, but being not limited to, octadecanol or hexadecanol may be used. The rate of the higher alcohol may be in the range of from approximately 30% to 70% by weight, preferably from approximately 40% to 60% by weight, with respect to the total dry weight.

The higher aliphatic acid may include a saturated or unsaturated aliphatic acid having from 14 to 20 carbon atoms, including, but being not limited to, myristic acid, palmitic acid, stearic acid, etc. The higher aliphatic acid may be contained at the rate of from approximately 1% to 30% by weight, preferably from approximately 5% to 20% by weight, with respect to the total dry weight.

The artificial pulmonary surfactant composition according to the present invention may further contain a neutral lipid including, but being not limited to, triacylglycerol, cholesterol, saponin or the like as an additional ingredient.

On the other hand, the proteins contained in the artificial pulmonary surfactant composition are considered to play a catalyzing action in order to permit the phospholipids to smoothly achieve the equilibrium between the single molecular membrane and the bimolecular molecular membrane (Perez-Gil, J., and Keough, K. M. W., *Biochim. Biophys. Acta*, 1998:1408, 203-217). As described above, the artificial pulmonary surfactant composition of the present invention is not limited to the above-mentioned lipid mixture system and the lipid mixture system to which a protein or a peptide is added as needed can also be used. As preferred examples of the artificial pulmonary surfactant peptides to be used for the present invention, there may be mentioned the peptides as invented by the present inventors and indicated in FIG. 1 (Japanese Patent Application Nos. 2003-98,607 and 2004-305,006; inventors: Lee Sannamu, Gosuke Sugihara, Isao Shibata and Ko Yukitake). As the details of the properties, effects, etc of these peptides are described in the specifications of the Japanese patent applications, they are incorporated herein as reference and constitute part of the description of this application. And the artificial pulmonary surfactant compositions of the instant invention may further contain the surfactant protein or surfactant peptide at the rate of from approximately 1% to 10% by weight, preferably from approximately 2% to 5% by weight with respect to the total dry weight.

The artificial pulmonary surfactant compositions according to the present invention may be prepared by admixing the above lipids with each other or the above lipids with the peptide or peptides at a predetermined rate. The artificial pulmonary surfactant compositions can be assessed for their surfactant activity by using a surface tension-area diagram. For comparative purposes, the measurements were conducted as a control for Exosurf® composed of the lipid system only and containing no peptide, which is to be used as a medicine for treating respiratory disorders, Surfaxin containing DPPC as a major ingredient and a synthetic peptide consisting of lysine (K) and leucine (L), and Surfacten®.

The artificial pulmonary surfactant compositions of the present invention can be formulated in accordance with conventional methods and may be applied in various dosage forms including, for example, solution, suspension, powder or the like. It may be stored in the form of aseptic preparations in a closed vessel such as vials or ampoules. The artificial pulmonary surfactant compositions may contain, as needed, a pharmacologically acceptable additive including, for example, a stabilizer, preservative, isotonic agent, buffering agent, suspending agent, antioxidant, surface active agent, etc. or a medicine including, for example, a bronchodilator, anti-allergy agent, anti-cancer agent, antibacterial agent, antiviral agent, etc.

When the artificial pulmonary surfactant composition of the present invention is applied as an agent for treating respiratory distress syndromes for example, the dose, usage and number of administration may be modified in accordance with the symptom of a patient and a combined therapy. The amount of one administration may be in the range of from 50 to 1,000 mg for a baby and from 500 to 5,000 mg for an adult. The dose may be adjusted so as to have a concentration of from 1.0 to 10.0% (w/v), for example, by suspending in distilled water, physiological saline, a physiologically acceptable buffer, etc. The artificial pulmonary surfactant composition can further be administered by injecting or spraying directly into the airway, for example, from one to ten times within 72 hours immediately after the occurrence of a respiratory disorder. It can also be inhaled directly when it is administered in a powdery form.

EXAMPLES

The present invention will be described in more detail by way of examples. It is to be understood herein that the present invention is not limited to the following examples in any respect and the following examples are described solely for the purpose to illustrate the invention.

1. Materials

As materials there were used the following: L-α-phosphatidylcholine (egg PC), a phospholipid purified from egg yolk (Avanti PolarLipids, Inc.); hydrogenated soy lecithin ("SLP White H", Tsuji Seiyu K.K., Japan); soy lecithin (fractional lecithin SLP-PC70, Tsuji Seiyu K.K., Japan), hydrogenated soy lecithin (prepared by hydrogenating soy lecithin SLP-PC70); egg yolk lecithin; and other lipids (Wako Jyunyaku K.K., Japan) as well as reagents (Wako Jyunyaku K.K., Japan). The peptides were synthesized by using an automatic synthesizer in the manner as described in literature (Kiyota, T., Lee, S., and Sugihara, G., *Biochemistry*, 35, 13196, 1996).

As a control, there were used the following: Exosurf® which is composed solely of a lipid system without any peptide and used as an agent for treating respiratory disorders; Surfaxin which is composed of DPPC as a major ingredient and contains a synthetic peptide consisting of lysine (K) and leucine (L); and Surfacten® (Mitsubishi Pharma Corp., Japan). Exosurf® and Surfaxin were each prescribed to yield a DPPC-1-hexadecanol-tyloxapol (84:16:0.25 w/w) system and a DPPC-PG-PA-KL4 (75:25:10:3 w/w) system, respectively.

2. Preparation of Samples (Lipid or Peptide-Lipid Mixture)

The following synthetic peptide, lipid, aliphatic acid and alcohol were weighed each at a predetermined amount and dissolved in a chloroform/methanol solution. The peptide was weighed and added as needed to the above lipid mixture sample so as to give an appropriate concentration (w/w). Nitrogen gas was then blown into the above lipid mixture solution or the peptide-containing mixture solution and the resulting solution was dried under reduced pressure to evaporate the organic solvents thoroughly and form a film coating on the wall surface of the vessel. To the vessel was added physiological saline, and the solution was stirred to give a suspension of the film coating. The suspension was used as a sample. As a control, Surfacten® was used by suspending 120 mg in 4 ml of physiological saline in accordance with its manual for application to the living body.

Figure 2A:
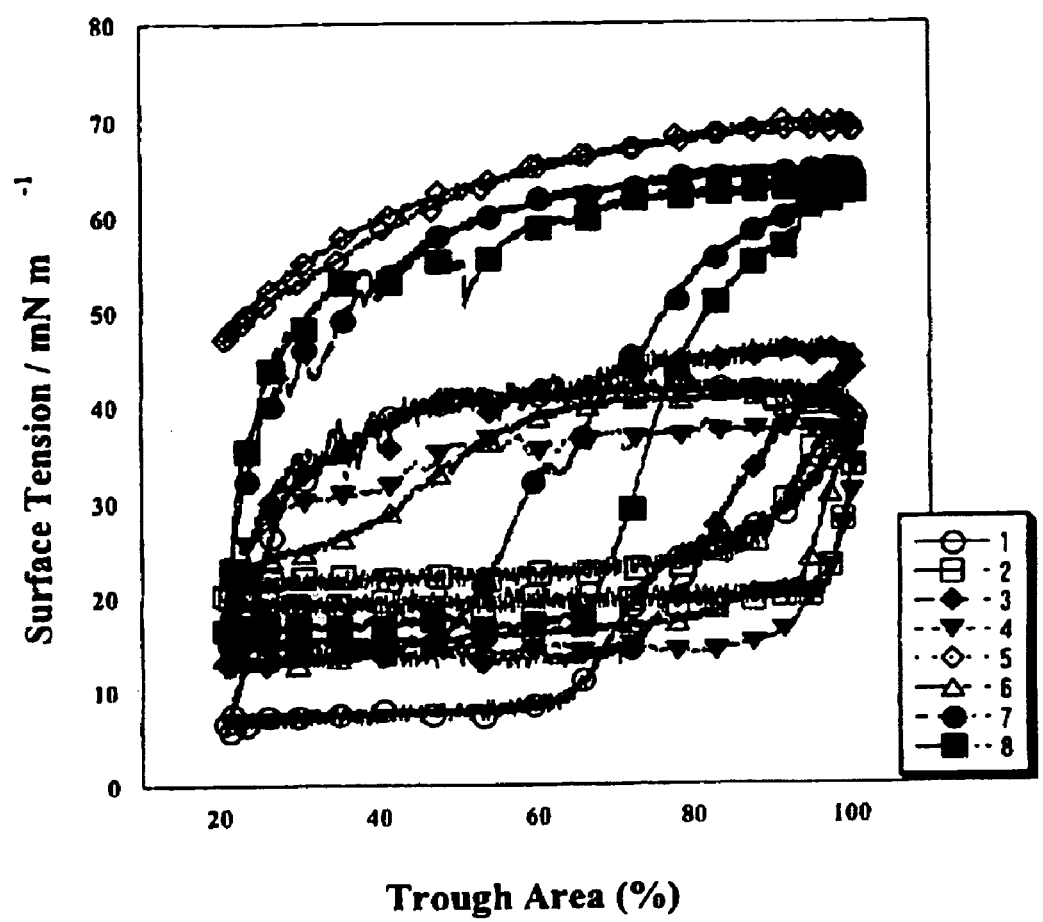
FIG. 2a shows a graph indicating the surface tension and the surface area curve of various lipid-peptide mixture systems.

(A) Samples to be Used for FIG. 2a:

| (1) Sample 1: | |
|---|---|
| Surfacten ® | |
| (2) Sample 2: | |
| 1-Octadecanol | 85% |
| Palmitic acid | 15% |
| (3) Sample 3: | |
| 1-Octadecanol | 35% |
| Phosphatidylcholine | 40% |
| Palmitic acid | 25% |
| (4) Sample 4: | |
| 1-Octadecanol | 35% |
| Egg yolk lecithin | 40% |
| Palmitic acid | 25% |
| (5) Sample 5: | |
| Phosphatidylcholine | 85% |
| Palmitic acid | 15% |
| (6) Sample 6: | |
| 1-Octadecanol | 30% |
| Phosphatidylcholine | 35% |
| Palmitic acid | 25% |
| Cholesterol | 10% |
| (7) Sample 7: | |
| 1-Octadecanol | 25% |
| Phosphatidylcholine | 40% |
| Palmitic acid | 25% |
| Triglycerol | 10% |
| (8) Sample 8: | |
| 1-Octadecanol | 30% |
| Phosphatidylcholine | 35% |
| Palmitic acid | 15% |

-continued

| | |
|---|---|
| Cholesterol | 10% |
| Triglycerol | 10% |

Figure 2B:
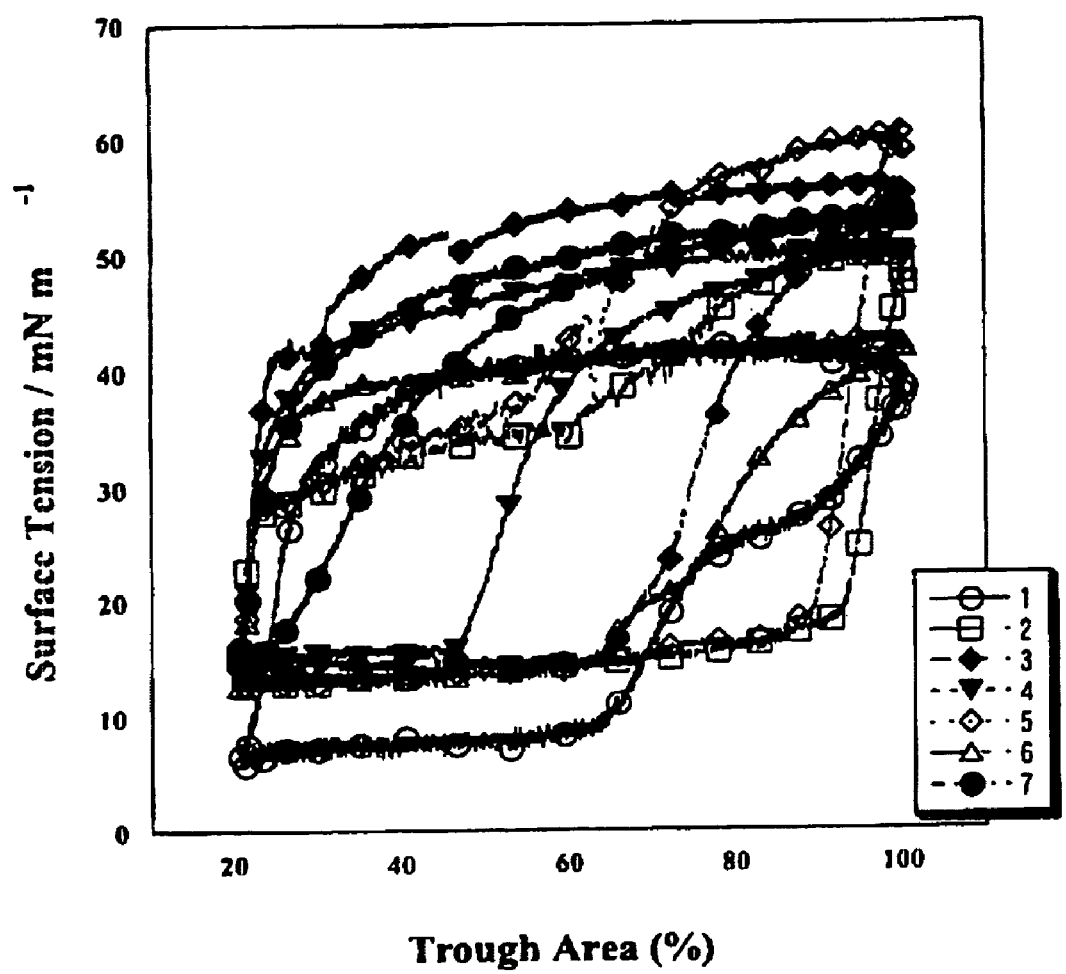
FIG. 2b shows a graph indicating the surface tension and the surface area curve in each of the composition ratios in various OD-egg PC-PA systems.

(B) Samples to be Used for FIG. 2b:

| (1) Sample 1: | |
|---|---|
| Surfacten ® | |
| (2) Sample 2: | |
| 1-Octadecanol | 70% |
| Phosphatidylcholine | 10% |
| Palmitic acid | 20% |
| (3) Sample 3: | |
| 1-Octadecanol | 40% |
| Phosphatidylcholine | 40% |
| Palmitic acid | 20% |
| (4) Sample 4: | |
| 1-Octadecanol | 10% |
| Phosphatidylcholine | 70% |
| Palmitic acid | 20% |
| (5) Sample 5: | |
| 1-Octadecanol | 80% |
| Phosphatidylcholine | 10% |
| Palmitic acid | 10% |
| (6) Sample 6: | |
| 1-Octadecanol | 40% |
| Phosphatidylcholine | 50% |
| Palmitic acid | 10% |
| (7) Sample 7: | |
| 1-Octadecanol | 10% |
| Phosphatidylcholine | 80% |
| Palmitic acid | 10% |

Figure 3:
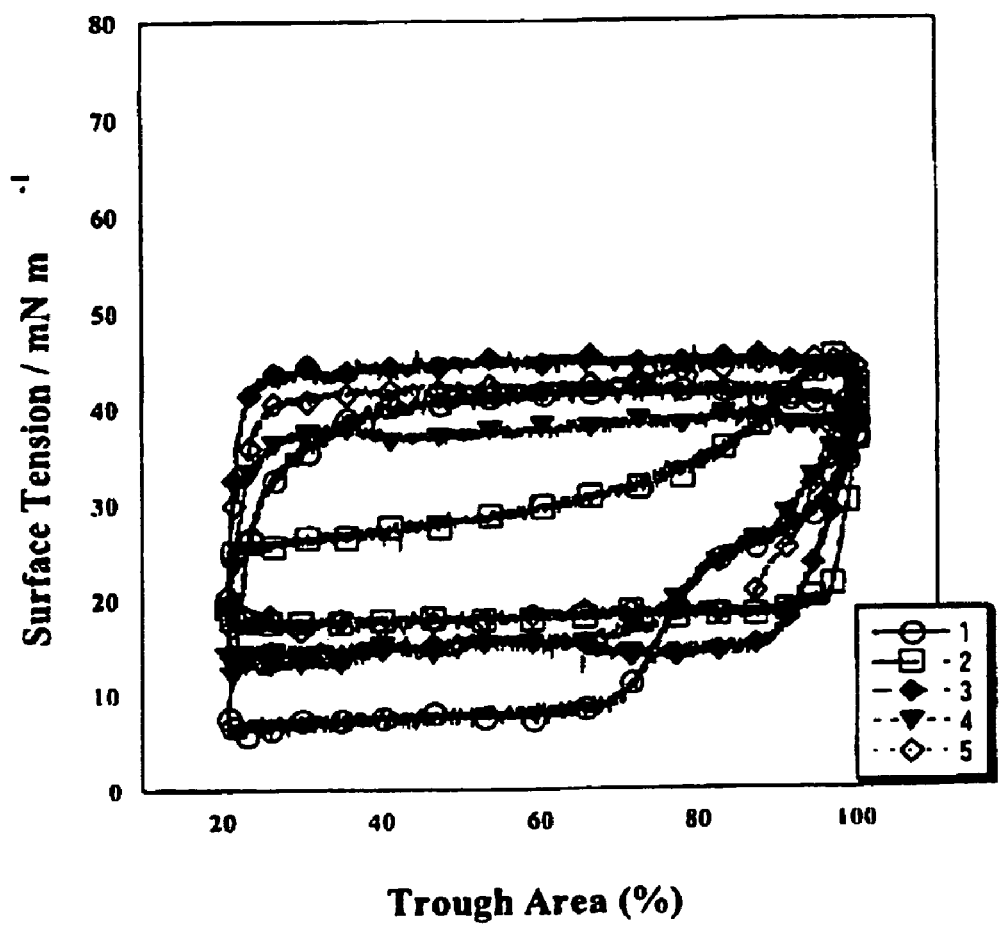
FIG. 3 shows a graph indicating the surface tension and the surface area curve in various lipid-peptide mixture systems.

(C) Samples to be Used for FIG. 3:

| (1) Sample 1: | |
|---|---|
| Surfacten ® | |
| (2) Sample 2: | |
| 1-Octadecanol | 85% |
| Palmitic acid | 10% |
| Peptide Hel 7-11-P24 | 5% |
| (3) Sample 3: | |
| 1-Octadecanol | 35% |
| Phosphatidylcholine | 40% |
| Palmitic acid | 20% |
| Peptide Hel 7-11-P24 | 5% |
| (4) Sample 4: | |
| 1-Octadecanol | 35% |
| Phosphatidylcholine | 40% |
| Palmitic acid | 20% |
| Peptide Hel 13-5 | 5% |
| (5) Sample 5: | |
| 1-Octadecanol | 35% |
| Phosphatidylcholine | 40% |
| Palmitic acid | 20% |
| KL4 | 5% |

Figure 4:
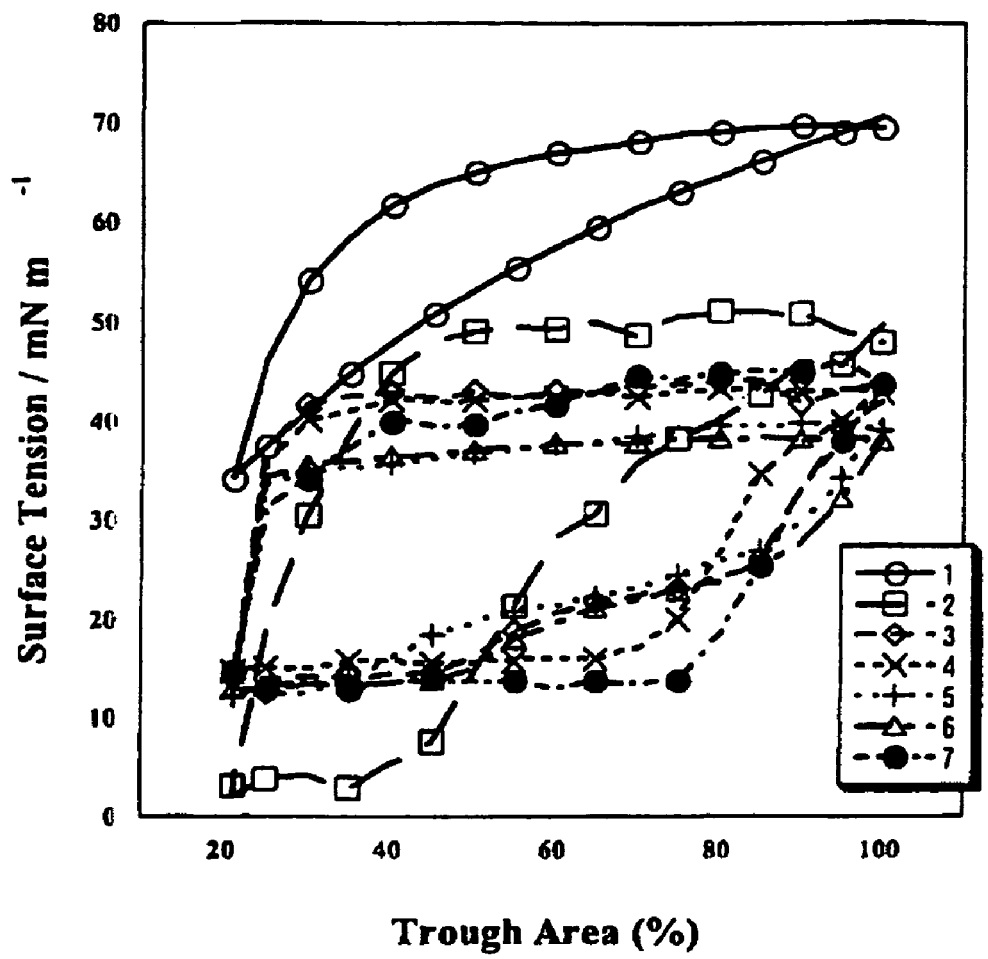
FIG. 4 shows an illustration indicating the result of a soy lecithin-lipid mixture system and its peptide mixture system.

(D) Samples to be Used for FIG. 4:

| | |
|---|---|
| (1) Sample 1: | |
| Exosurf® | |
| (2) Sample 2: | |
| Surfaxin | |
| (3) Sample 3: | |
| Hydrogenated soy lecithin PC70 | 40% |
| Soy lecithin PC70 | 40% |
| Palmitic acid | 20% |
| (4) Sample 3: | |
| Hydrogenated soy lecithin | 40% |
| Soy lecithin PC70 | 40% |
| Palmitic acid | 20% |
| (5) Sample 5: | |
| Hydrogenated soy lecithin | 40% |
| Soy lecithin PC70 | 40% |
| Palmitic acid | 17.5% |
| Peptide Hel 13-5 | 2.5% |
| (6) Sample 6: | |
| Hydrogenated soy lecithin PC70-H | 40% |
| Soy lecithin PC70 | 40% |
| Palmitic acid | 17.5% |
| Peptide Hel 13-5 | 2.5% |
| (7) Sample 7: | |
| 1-Octadecanol | 35% |
| Hydrogenated soy lecithin | 40% |
| Palmitic acid | 20% |
| Peptide Hel 13-5 | 5% |

3. Processes for Formation and Experiments of Surface Tension—Area Diagram

The surface tension was measured with Acoma Wilhelmy Balance (Acoma Medical Industry Co., Ltd., Japan). A Teflon® water vessel (78×138×30 mm) was filled with physiological saline forming a closed liquid surface. The air-liquid interface of the liquid surface was developed with 20 µl of the lipid mixture and allowed to stand for 3 minutes to permit the lipid mixture to naturally spread thereon. A variation in the surface tension during this period of time was recorded as a surface spreading rate with a platinum plate hanging vertically in the vessel. The single molecular membrane formed in 3 minutes was recorded as a surface area by repeatedly spreading and compressing alternately at the speed of 3 minutes per cycle in the range from the maximum area of 45 cm$^2$ to the minimum area of 9 cm$^2$. The surface tension acting onto the platinum plate was converted into electrical signals with a force converter, and the electrical signals were automatically recorded continually with an X-Y recorder, together with the variation in the surface area. The recording was continued until no variation could be recognized any longer. The figures in the drawing are represented on the basis of the seventh cycle.

4. Tests for Pulmonary Surfactant-Deficient Models by Irrigation of the Lung of Rat Mature rats each having a body weight of approximately 500 grams were subjected to tracheotomy and the lung of each rat was irrigated with warm physiological saline to form a pulmonary surfactant-deficient model. The rat model was then placed under artificial ventilation of 100% oxygen and each of two artificial pulmonary surfactant compositions of this invention was administered in order to make investigations for an effect on the prolongation of life and compliance: the first one being an artificial pulmonary surfactant composition of the peptide type composed of hydrogenated soy lecithin-soy lecithin PC70-PA-peptide Hel 13-5 (40:40:17.5:2.5) and the second one being an artificial pulmonary surfactant composition of the non-peptide type composed of hydrogenated soy lecithin-soy lecithin PC70-PA (40:40:20). As controls, there were used three pulmonary surfactants: Surfacten® derived from the bovine pulmonary surfactant and extensively applied clinically, Surfaxin and Exosurf®, and one (physiological saline, 2 ml) with no pulmonary surfactant administered. The method for the suspension and the amount of administration of each surfactant composition were followed in accordance with the method for the administration of Surfacten® to the living body. A suspension of 30 mg/ml was prepared by adding physiological saline, and 1 ml of the suspension was administered through a transtracheal route. As a parameter for the pulmonary function, a pulmonary compliance (an amount of ventilation/a difference of airway pressures) was measured before irrigation, after irrigation but immediately before administration of the surfactant, 30 minutes after administration of the surfactant, 60 minutes thereafter, 90 minutes thereafter, 120 minutes thereafter, 150 minutes thereafter and 180 minutes thereafter. The irrigation of the rat lung was carried out until a compliance of approximately 0.60 ml/cm H$_2$O before irrigation reached approximately 0.2 ml/cm H$_2$O and the formation of a pulmonary surfactant-deficient rat model was confirmed. After confirmation, the tests for administration of various surfactants were then conducted by administering each surfactant to a group of six or more rat models.

Results of Experiments

The surface tension of the pulmonary surfactant is characterized by a hysteresis curve drawn upon the measurement for the surface tension-area curve with the Wilhemy surface tensometer. Generally speaking, it is considered that a better pulmonary surfactant activity is shown as the speed of a decrease of the surface tension at the time of compression is faster or as the capability of automatically spreading the surface tension is faster. In other words, the pulmonary surfactant activity is considered to be better as the area forming a hysteresis curve is greater or as a surface tension at the time of compression is smaller. As shown in FIGS. 2 and 3, the minimal surface tension of Surfacten® at the time of compression was found to be 7 mNm$^{-1}$ or the maximal surface tension thereof at the time of each spreading is found 45 mNm$^{-1}$.

FIGS. 2a and 2b show the result of the surface tension—area curves for the artificial pulmonary surfactant compositions having different kinds of lipid formulations as compared with Surfacten® as a control. As shown in FIG. 2, no better hysteresis curves were obtained for the two-component systems: OD-PA (85:15), egg PC-PA (85:15) and OD-PC (40:60). A three-component composition, i.e. OD-egg PC-PA (35:40:25), gave a favorable hysteresis curve although its minimal surface tension (13 mNm$^{-1}$) is not comparable to that of Surfacten® (see line 3 of FIG. 2). No improvements were shown by the addition of cholesterol (Ch) and saturated acyl-triglycerol (TG) to the OD-egg PC-PA composition or its mixture thereof.

As a good result was obtained for the OD-egg PC-PA composition, further experiments were conducted for the systems in which the compositions were modified (FIG. 2b). The systems where OD and egg PC were contained in more amounts gave no better results than Surfacten® (see lines 2, 4, 5 and 7 of FIG. 2b). On the other hand, the systems which contained OD and egg PC at the amounts closer thereto showed good results (see lines 3 and 6 of FIG. 2b). It was also found that the OD-egg PC-PA (40:40:20) system containing PA by 20% gave a surface tension pressure value at the time of expanding greater than the OD-egg PC-PA (40:50:10) system containing 10% of PA, resulting in a greater area drawn by the hysteresis curve. Generally speaking, it is said that a greater area of the hysteresis curve can give better results, however, the surface tension at the time of expanding is not clear regarding the relationship in vivo.

FIG. 3 shows the results of the lipid-peptide mixture systems. Better curves were generally obtained for the OD-egg-PA systems in which various peptides were added. For example, little difference was shown among peptides Hel 7-11-P24, P24, Hel 13-5 and so on. Surfaxin currently under phase 3 of the clinical study gave the results similar to the other peptides.

FIG. 4 shows the results of the soy lecithin-lipid mixture system and the peptide mixture system thereof as well as Exosurf® and Surfaxin as controls. It is interesting to note that the soy lipid mixture system gave a favorable hysteresis curve as the OD-egg PC-PA system, while the OD-hydrogenated soy PC-PA (35:40:25) system did not give a good hysteresis curve. It is also interesting to note that the system in which the peptide was added to hydrogenated soy PC had a somewhat weaker spreading force at the time of expanding, but a decrease of the surface tension at the time of compressing was better than that of Surfacten® (see line 5 of FIG. 5), while neither Exosurf® nor Surfaxin gave any curve like Surfacten®.

As noted above, some lipid mixture systems gave a hysteresis curve more favorable as a pulmonary surfactant than that of Surfacten®. This reveals that the lipid mixture system alone can have a sufficiently high pulmonary surfactant activity even if no peptide or protein is contained. Among them, certain systems were found that the minimal value of the surfactant activity at the time of compressing was somewhat higher than Surfacten®, however, a more rapid decrease in the surface tension was recognized than Surfacten®.

5. Results of Experiments for Recovery of the Pulmonary Function Using Rats with the Lung Irrigated A review has been made for the effects on the pulmonary function using a pulmonary surfactant-deficient rat model formed by irrigating the lung of a rat weighing approximately 500 grams with warm physiological saline. The artificial pulmonary surfactant of the present invention was administered and measured for the prolongation of life and pulmonary compliance (an amount of ventilation/a difference of airway pressures) before irrigation, immediately before administration of the surfactant but after irrigation, immediately after administration of the surfactant, 30 minutes, 60 minutes, 90 minutes, 120 minutes, 150 minutes and 180 minutes thereafter. Seven kinds of the pulmonary surfactant compositions were used for these experiments as follows: peptide-containing pulmonary surfactant systems (OD-egg PC-PA-peptide Hel 13-5 (35:40:20:5) and hydrogenated soy lecithin-soy lecithin PC70-PA-peptide Hel 13-5 (40:40:17.5:2.5)); pulmonary surfactant systems containing no peptide (OD-egg PC-PA (35:40:25) and hydrogenated soy lecithin-soy lecithin PC70-PA (40:40:20)); Surfacten®; Surfaxin; and Exosurf®. As a control in which no pulmonary surfactant was contained, 2 ml of physiological saline was used. Each of the pulmonary surfactants was administered in the dose of 60 mg (30 mg/ml) (see FIG. 5).

It is to be noted herein, however, that the irrigation of the lung caused to reduce the pulmonary compliance of all the rats used therefor to approximately 0.2 ml/cm $H_2O$. Further, it is noted that the pulmonary compliance of the rats in the group with no surfactant administered was continually reduced after irrigation resulting to death of all rats within 1 hour after administration.

For the rats in the group where Surfacten® containing the pulmonary surfactant protein was administered, the pulmonary compliance elevated to 0.255 ml/cm $H_2O$ immediately after administration and to 0.288 ml/cm $H_2O$ within 30 minutes thereafter, followed maintaining the pulmonary compliance at approximately 0.3 ml/cm $H_2O$ till 3 hours when the experiment was finished. For the rats in the group where Surfaxin containing the peptide was administered, the pulmonary compliance was reduced to 0.179 ml/cm $H_2O$, but recovered to 0.248 ml/cm $H_2O$ within 30 minutes after administration and to 0.279 ml/cm $H_2O$ within 60 minutes thereafter, followed by reducing again to 0.24 ml/cm $H_2O$ within 90 minutes thereafter and to 0.237 ml/cm $H_2O$ within 3 hours thereafter when the experiment was finished (see FIG. 6). For the rats in the group where the pulmonary surfactant composition containing a peptide according to this invention (hydrogenated soy lecithin-soy lecithin PC70-PA-peptide Hel 13-5 (40:40:17.5:2.5)) was administered, the pulmonary compliance was increased to 0.237 ml/cm $H_2O$ immediately after administration, to 0.275 ml/cm $H_2O$ within 30 minutes thereafter and to 0.268 ml/cm $H_2O$ within 60 minutes thereafter, followed by reducing down to 0.26 ml/cm $H_2O$ within 90 minutes thereafter and increasing again to 0.3 ml/cm $H_2O$ in 3 hours when the experiment was finished. It can further be noted that the recovery of the pulmonary compliance in 150 minutes immediately after administration was recovered to some extent to a level somewhat poorer than Surfacten®, but recovered to a level equal thereto in 180 minutes thereafter. A comparison with Surfaxin revealed that the artificial pulmonary surfactant composition of this invention demonstrated better pulmonary compliances during all the measurement period of time. The OD-egg PC-PA-Hel 13-5 composition demonstrated a somewhat weaker recovery of the pulmonary compliance as compared to the soy lipid system, but a better recovery than Surfaxin.

Figure 5A:
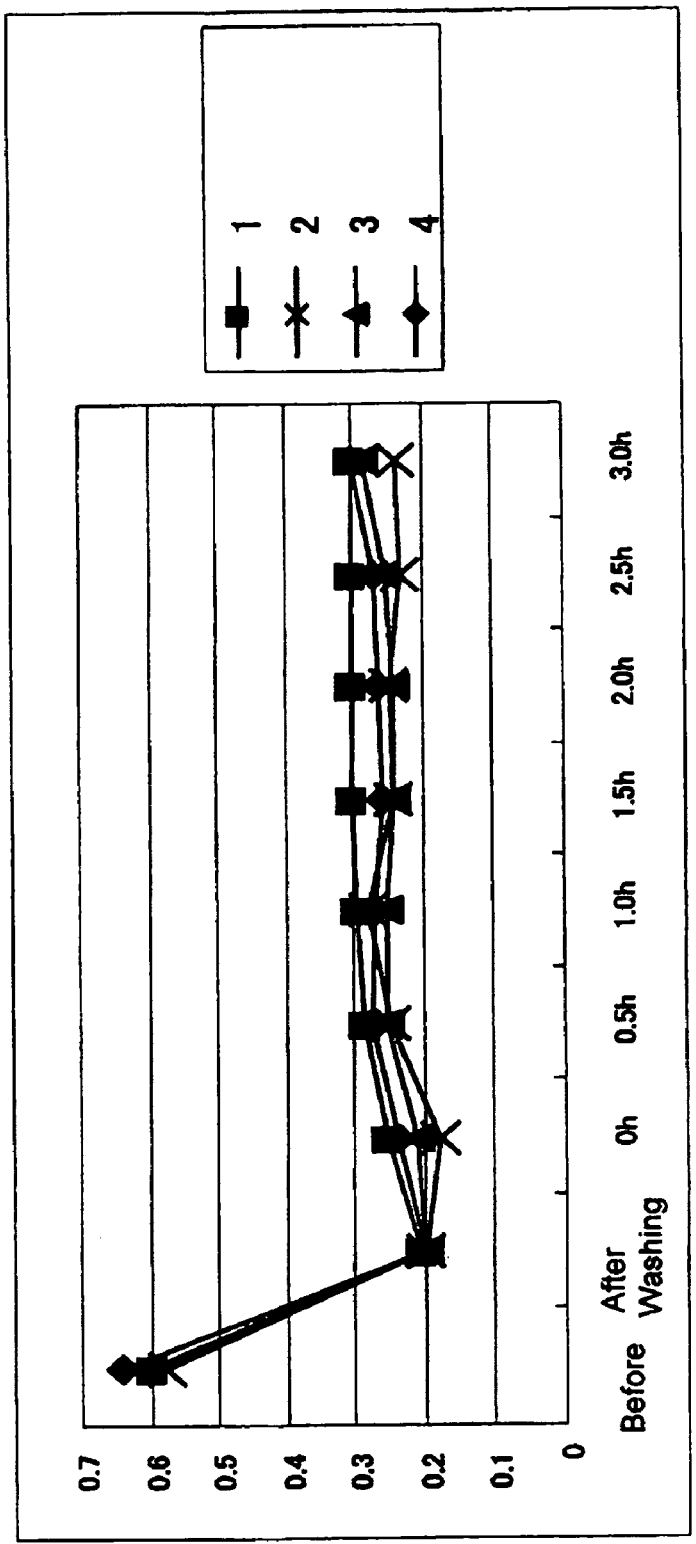
FIG. 5a shows an illustration indicating the result of an experiment for the recovery of the pulmonary function using rats with the lung irrigated.

Regarding the systems in which no peptide was contained, Exosurf® decreased the pulmonary compliance to 0.15 ml/cm $H_2O$ immediately after its administration and sustained it at 0.165 ml/cm $H_2O$ in 30 minutes thereafter and at 0.17 ml/cm $H_2O$ in 60 minutes et seq. thereafter (FIG. 5b). On the other hand, the OD-egg PC-PA composition of this invention did not cause a decrease of the pulmonary compliance and had a compliance of 0.198 ml/cm $H_2O$ immediately after its administration, increasing to 0.211 ml/cm $H_2O$ in 30 minutes thereafter and then reducing to 0.18 ml/cm $H_2O$ in 60 minutes thereafter, followed by increasing to 0.20 ml/cm $H_2O$ in 90 minutes thereafter and indicating a compliance of approximately 0.21 ml/cm $H_2O$ after 90 minutes et seq. It can be further noted that the pulmonary surfactant composition of this invention which does not contain any peptide demonstrated better results than Exosurf® containing no peptide during all the measurement period of time and, further, that the pulmonary compliance in 3 hours after administration was 0.237 ml/cm $H_2O$. The system composed of the hydrogenated soy lecithin-soy lecithinPC70-PA demonstrated similar results.

From the test results as described above, the soy lipid-peptide mixture system showed somewhat weaker effects on improvements of the pulmonary functions in rats models deficient in pulmonary surfactant for 150 minutes immediately after administration, but demonstrated the pulmonary functions as high as Surfacten® containing natural apoproteins derived from the bovine pulmonary surfactants in 180 minutes after administration. Further, it showed better functions than Surfaxin containing the peptide during the whole period of experimental time. In addition, the soy lipid mixture system containing no peptide demonstrated better functions than Exosurf® for the whole period of experimental time.

INDUSTRIAL APPLICABILITY

As the mixture system according to this invention can be prepared at very lower costs as compared with Surfacten®, it can be applied not only to RDS and ADRS, but also to mitigating or preventing severe respiratory distress at the terminal stage of pulmonary cancers, removing phlegm, relieving the symptom of respiratory difficulties caused by asthma and so on. Further, as the artificial pulmonary surfactant compositions of this invention are composed of a completely man-made pulmonary surfactant that does not use any protein derived from a living thing such as the bovine lung, etc. as a raw material, it can be relieved from the problems with unknown infection, bovine spongiform encephalopathy, allergy, etc. caused by the pulmonary surfactant derived from the bovine lung. In addition, the lipids to be used for the artificial pulmonary surfactant compositions according to this invention are all authorized to be used for use as a medicine. Therefore, it is considered that no problem with toxicity will be caused to occur. From the above findings, the artificial pulmonary surfactant compositions of this invention can be expected to be applied as a medicine for treating a wide variety of pulmonary diseases.

What is claimed is:

1. An artificial pulmonary surfactant composition comprising a lipid mixture composed of a phospholipid selected from the group consisting of dipalmitoyl-L-α-phosphatidylcholine (DPPC), egg yolk lecithin and soy lecithin, a higher alcohol selected from the group consisting of a saturated or unsaturated aliphatic, alcohol having from 14 to 20 carbon atoms or a saturated or unsaturated aliphatic, higher aliphatic amine having from 14 to 20 carbon atoms, and a higher aliphatic acid selected from the group consisting of a saturated or unsaturated aliphatic acid having from 14 to 20 carbon atoms, wherein said composition further comprises a peptide selected from the group consisting of:

NH2-KLLKLLLKLWLKLLKLLL-COOH (SEQ. ID. NO: 1),

NH2-KLLKLLLKLWKKLLKLLK-COOH (SEQ. ID. NO: 2) and

NH2-KKLKKLLKKWKKLLKKLK-OH (SEQ. ID. NO: 3).

2. The artificial pulmonary surfactant composition as claimed in claim 1, wherein said phospholipid is contained in an amount of 20% to 60% by weight, said higher alcohol is contained in an amount of 30% to 70% by weight, and said higher aliphatic acid is contained in an amount of 1% to 30% by weight, each by weight with respect to the total dry weight of the composition.

3. The artificial pulmonary surfactant composition as claimed in claim 1, wherein said phospholipid is contained in an amount of 30% to 50% by weight, said higher alcohol is contained in an amount of 40% to 60% by weight, and said higher aliphatic acid is contained in an amount of 5% to 20% by weight, each by weight with respect to the total dry weight of the composition.

4. The artificial pulmonary surfactant composition as claimed in claim 1, wherein said peptide is further contained in an amount of 1% to 10% by weight with respect to the total dry weight of the composition.

5. The artificial pulmonary surfactant composition as claimed in claim 1, wherein said protein or peptide is further contained in an amount of 2% to 5% by weight with respect to the total dry weight of the composition.

6. The artificial pulmonary surfactant composition as claimed in claim 1, wherein said higher alcohol is octadecanol.

7. The artificial pulmonary surfactant composition as claimed in claim 1, wherein said higher aliphatic acid is palmitic acid.

8. An artificial pulmonary surfactant composition comprising a lipid mixture composed of a phospholipid selected from the group consisting of dipalmitoyl-L-α-phosphatidylcholine (DPPC), egg yolk lecithin and soy lecithin, in an amount of 20% to 60% by weight, octadecanol in an amount of 30% to 70% by weight, and palmitic acid in an amount of 1% to 30% by weight, each by weight with respect to the total dry weight of the composition, wherein said composition further comprises a peptide selected from the group consisting of:

NH2-KLLKLLLKLWLKLLKLLL-COOH (SEQ. ID. NO: 1),

NH2-KLLKLLLKLWKKLLKLLK-COOH (SEQ. ID. NO: 2) and

NH2-KKLKKLLKKWKKLLKKLK-OH (SEQ. ID. NO: 3).

9. The artificial pulmonary surfactant composition as claimed in claim 2, wherein said phospholipid is contained in an amount of 30% to 50% by weight, said higher alcohol is contained in an amount of 40% to 60% by weight, and said higher aliphatic acid is contained in an amount of 5% to 20% by weight, each by weight with respect to the total dry weight of the composition.

10. The artificial pulmonary surfactant composition as claimed in claim 8, wherein said phospholipid is contained in an amount of 30% to 50% by weight, said octadecanol is contained in an amount of 40% to 60% by weight, and said palmitic acid is contained in an amount of 5% to 20% by weight, each by weight with respect to the total dry weight of the composition.

* * * * *